(12) United States Patent
Crainich et al.

(10) Patent No.: US 8,935,974 B2
(45) Date of Patent: Jan. 20, 2015

(54) OSCILLATING ROD CUTTER

(75) Inventors: Lawrence Crainich, Charlestown, NH (US); Joseph E. Trabka, Charlestown, NH (US)

(73) Assignee: Vermont Instrument Makers, Occidental, CA (US)

( * ) Notice: Subject to any disclaimer, the term of this patent is extended or adjusted under 35 U.S.C. 154(b) by 855 days.

(21) Appl. No.: 12/942,146

(22) Filed: Nov. 9, 2010

(65) Prior Publication Data

US 2011/0107601 A1 May 12, 2011

Related U.S. Application Data

(60) Provisional application No. 61/259,253, filed on Nov. 9, 2009.

(51) Int. Cl.
| | | |
|---|---|---|
| *B23D 17/04* | (2006.01) | |
| *B23D 29/00* | (2006.01) | |
| *B26D 3/16* | (2006.01) | |
| *A61B 17/88* | (2006.01) | |
| *B23D 29/02* | (2006.01) | |

(52) U.S. Cl.
CPC .............. *B26D 3/16* (2013.01); *A61B 17/8863* (2013.01); *B23D 29/023* (2013.01)
USPC .......................... 83/13; 30/92; 30/95; 30/194

(58) Field of Classification Search
CPC ........ B23D 17/00; B23D 17/02; B23D 17/04; B23D 29/00; B23D 29/002; B23D 29/02; B23D 29/023; B23D 21/00; B23D 21/06; B23D 21/10; B26D 3/16; B26D 3/166; B26D 3/169; B26D 3/162; B26D 3/167
USPC ................. 30/92–95, 97, 173, 194, 217–220; 83/13, 199, 196, 694; 606/1, 17, 79
See application file for complete search history.

(56) References Cited

U.S. PATENT DOCUMENTS

| 690,083 | A | * | 12/1901 | Stolpe | ............................. 83/199 |
| 3,494,233 | A | * | 2/1970 | Kojima | ........................... 83/199 |
| 5,988,027 | A | * | 11/1999 | Lenox | ................ 83/13 |
| 6,058,820 | A | * | 5/2000 | Rinner | ............................ 83/200 |
| 8,127,454 | B1 | * | 3/2012 | Gao | .................................. 30/92 |

* cited by examiner

*Primary Examiner* — Phong Nguyen
(74) *Attorney, Agent, or Firm* — Bachman & LaPointe, PC

(57) ABSTRACT

A rod cutter apparatus includes a rod holding plate having a rod opening for receiving a rod to be cut; a cutting member having a central opening defined by a cutting edge, the central opening being substantially aligned with the rod opening; and a drive assembly connected between the rod holding plate and the cutting member to cause oscillation of the cutting member relative to the rod holding plate, wherein oscillation of the cutting member relative to the rod holding plate cuts a rod in the rod opening.

15 Claims, 14 Drawing Sheets

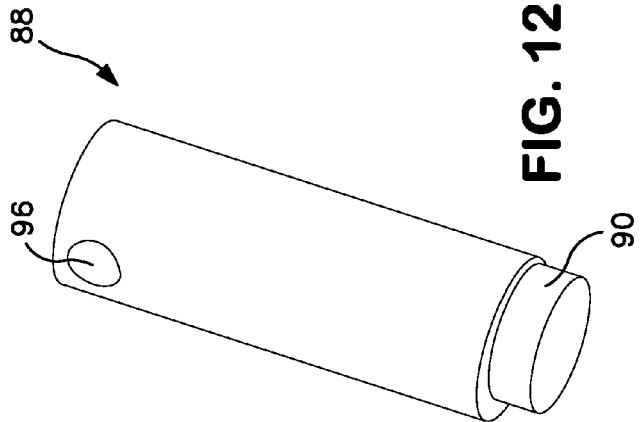
FIG. 12
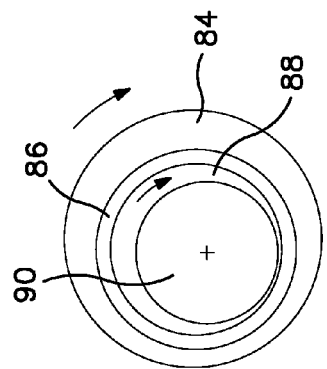
FIG. 14
FIG. 11
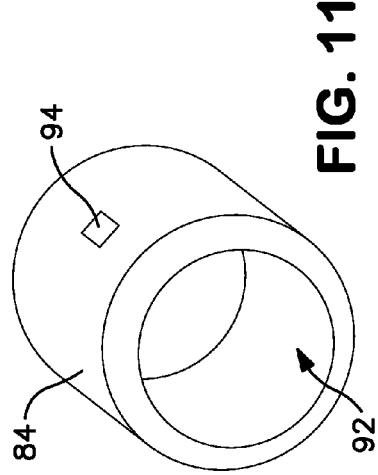
FIG. 13

OSCILLATING ROD CUTTER

CROSS-REFERENCE TO RELATED APPLICATION

This application claims the benefit of the filing date of U.S. Provisional Application 61/259,253, filed Nov. 9, 2009.

BACKGROUND OF THE INVENTION

This invention relates to a device for cutting rods, more particularly, to a rod cutter that is useful in cutting rods that are used in the medical arts. These rods may be the implanting rods, such as but not limited to, rods implanted or implantable in a body for spinal fixation, bone fixation and the like.

Spinal implants involve the use of rods, which are typically too long and need to be cut down to fit individual needs. Rod cutters may be used for this purpose and are typically arranged to have a supporting base that rests upon a tabletop or the like, and a relatively long handle is pivoted to the base for actuating cutters, which sever a rod to be used in the spinal implant. In that endeavor, the goal is to provide a rod cutter with sufficient mechanical advantage or cutting leverage so that the user can sufficiently manipulate the pivotal handle for severing the rod with a minimum of effort, and for cutting rods of varying cross-sectional sizes.

Another tool used for cutting rods is the medical equivalent of a commercial bolt cutter. These commercial bolt cutters are primarily made of stainless steel. Neither concept above is conducive to cutting the rods while they are in place in the body of a patient during a surgical procedure. As a result, the rods are typically installed in the body, marked for length, cut to the marked length away from the patient using a table mounted rod cutter, and then replaced back into the body.

Due to the use of leverage as the cutting force, such as with conventional bolt cutters, and the need for a sturdy mount, such as a tabletop mount, prior art rod cutters lack mobility and they lack the required extreme force to cut strong metals, such as titanium.

As a result, there is a need for a rod cutter that allows for a greater degree of mobility and increased cutting strength. There is a need for a rod cutter that is sufficiently mobile to be used adjacent the patient or with a portion of the rod cutter extending into the incision to cut a rod to be or which has been implanted.

SUMMARY OF THE INVENTION

The present disclosure provides a rod cutter which produces forces sufficient to cut durable rods such as rods made of titanium, and which does not require a cumbersome base or mount. The rod cutter employs a series of gears, eccentric members and plate members that drive a circular blade to oscillate relative to a rod to be cut. The oscillating rod cutter exhibits superior cutting strength, through mechanical gearing advantages, without producing burrs or sharp ends on cut surfaces of the rods. The oscillating rod cutter of the present disclosure, while useful specifically in the surgical arts, can also find beneficial use in differing environments and in mechanical arts in general.

The present disclosure also provides a method of cutting a rod using the oscillating rod cutter of the present invention.

In accordance with the present disclosure, a rod cutting apparatus is provided, which comprises a rod holding plate having a rod opening for receiving a rod to be cut; a cutting member having a central opening defined by a cutting edge, the central opening being substantially aligned with the rod opening; and a drive assembly connected between the rod holding plate and the cutting member to cause oscillation of the cutting member relative to the rod holding plate, wherein oscillation of the cutting member relative to the rod holding plate cuts a rod in the rod opening.

A method for cutting a rod using the rod cutting apparatus of the present invention is also provided.

BRIEF DESCRIPTION OF THE DRAWINGS

A detailed description of preferred embodiments of the present invention follows, with reference to the attached drawings, wherein:

FIG. 11 illustrates a sleeve having an eccentric bore according to the invention;

FIG. 12 illustrates a drive shaft having an eccentrically positioned end according to the invention;

FIGS. 13 and 14 illustrate the drive shaft assembly from a bottom view, showing movement of the eccentrically positioned end from a starting point to a displaced point;

DETAILED DESCRIPTION

The invention relates to an apparatus for cutting rods, and more particularly to an apparatus which utilizes an oscillating blade to cut rods which can be otherwise difficult to cut, such as titanium rods used in surgical procedures.

Hereinafter the term "rod" is used to refer to any one or all of the following terms: metal rod, plastic rod, an article of the appropriate size and shape, i.e. an elongated member and any article that may benefit from or be cut by this novel rod cutter.

Figure 1:
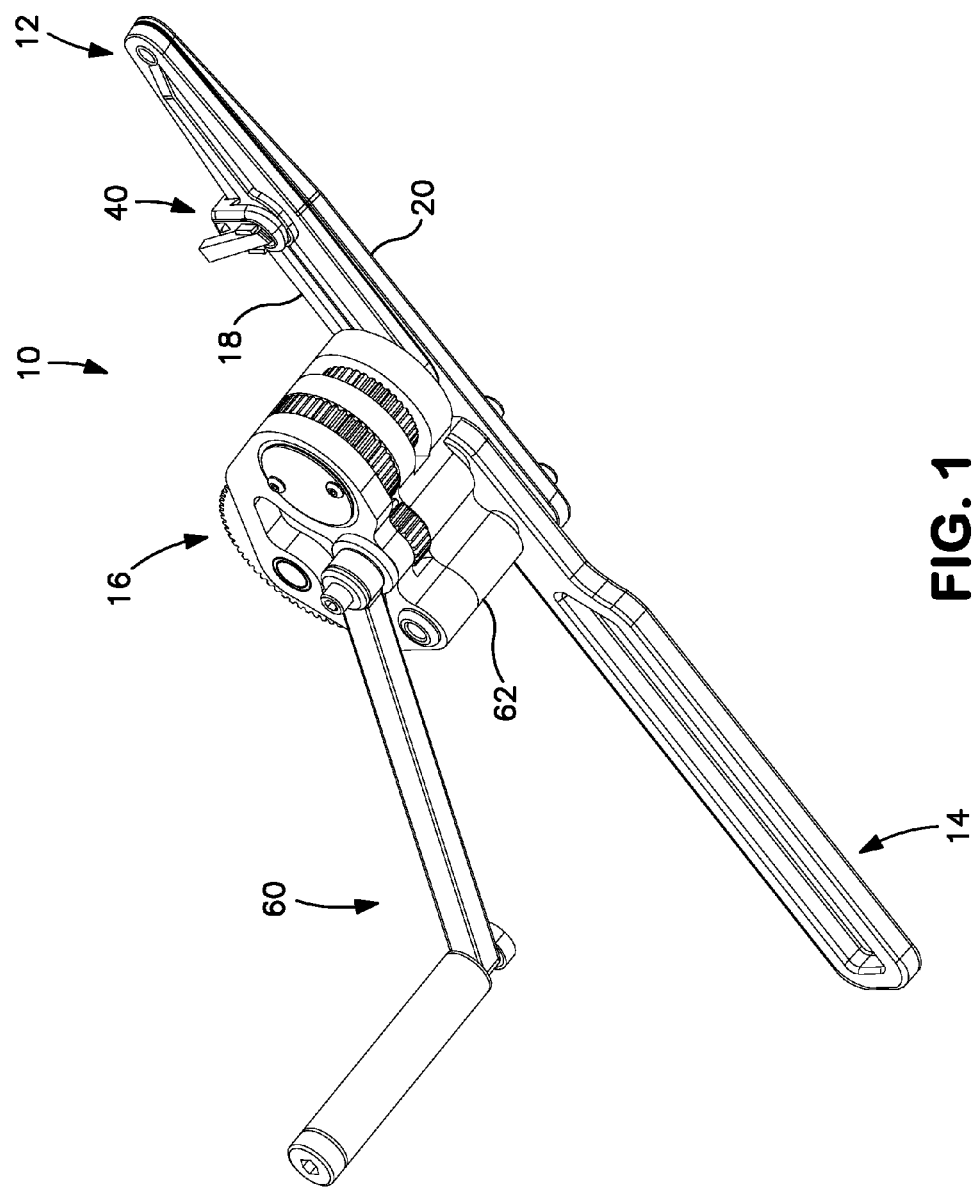
FIG. 1 is a perspective view of a rod cutting apparatus according to the invention.

FIG. 1 illustrates a rod cutter apparatus 10 according to the invention which will be referred to herein as rod cutter 10 or apparatus 10. Rod cutter 10 according to the invention has a cutting assembly 12 for holding and cutting a rod, a handle 14 and a drive assembly 16 for driving movement of a cutting blade relative to a rod held in cutting assembly 12 as will be discussed further below.

Also as will be further discussed below, rod cutter 10 cuts rods by generating an oscillating movement of a ring-shaped blade relative to the rod, wherein the oscillating movement is of gradually increasing magnitude. This gradually increasing oscillation generates a very large cutting force which cleanly and effectively cuts rods made from very durable materials such as titanium and the like.

Figure 2:
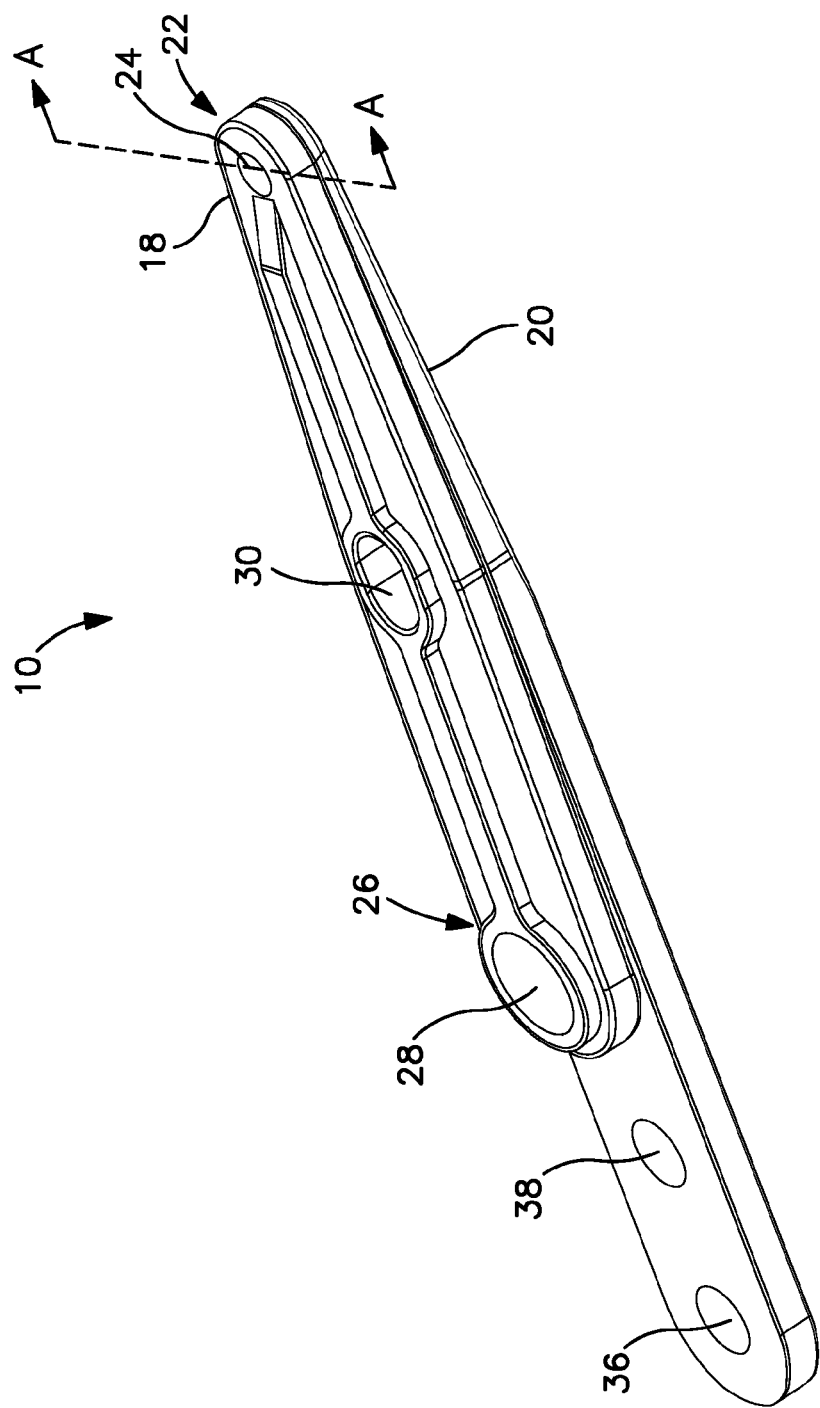
FIG. 2 is a perspective view of the oscillating plate structure of the apparatus according to the invention.

Referring also to FIG. 2, rod cutter 10 preferably has two plate members 18, 20 which are movable one relative to the other. One plate 20 holds the rod to be cut, while the other plate 18 holds the blade and can be oscillated relative to plate 20 so as to generate the cutting movement of the blade relative to the rod as desired.

Plate 18 is advantageously an elongate member having a distal end 22 having an opening 24, a proximal end 26 having an opening 28 for receiving drive assembly 16, and a central opening 30 for moveable fastening relative to plate 20.

Figure 3:
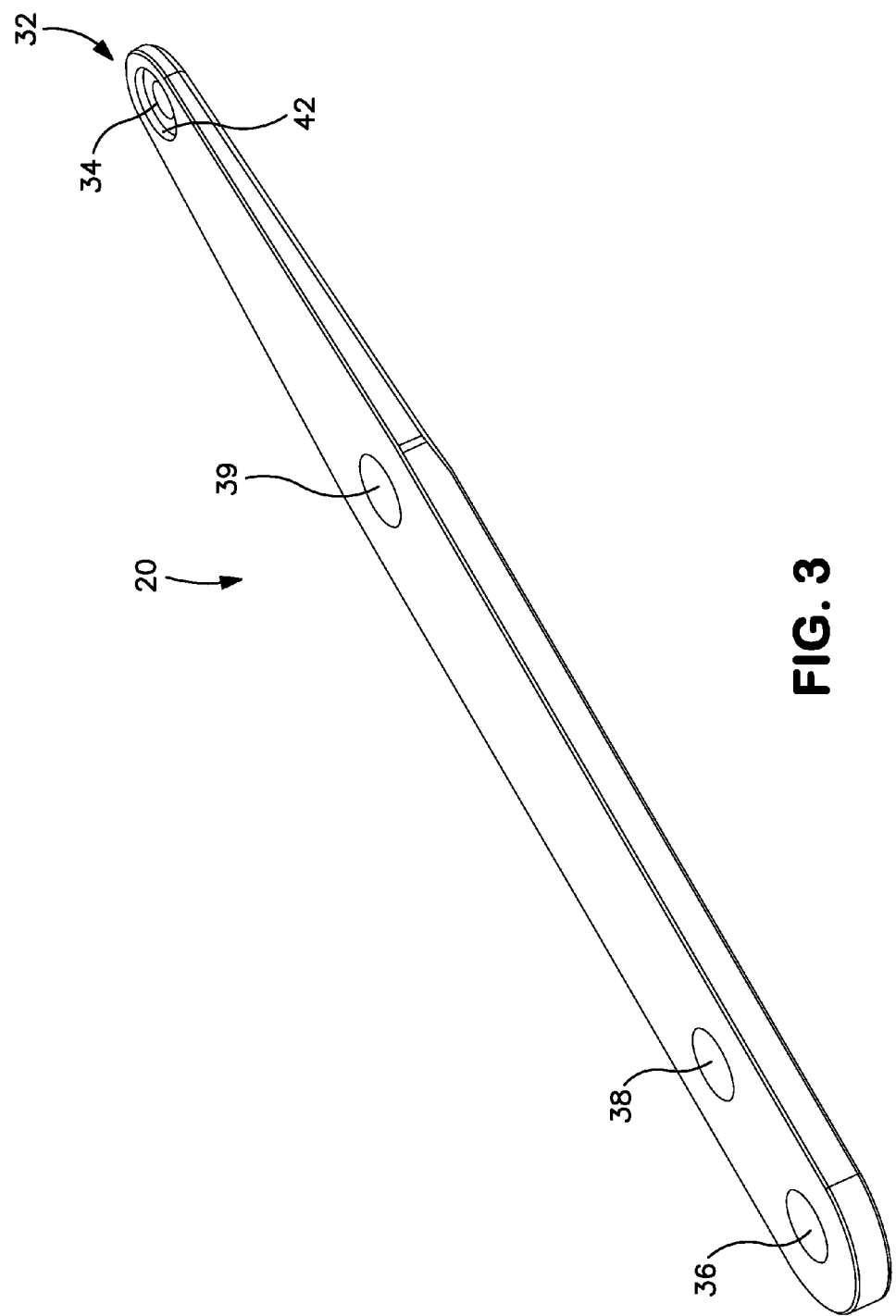
FIG. 3 is a perspective view of one of the plates of the apparatus of the present invention.

Plate 20 is also illustrated in FIG. 3, and can be an elongate member having a distal end 32 having an opening 34 for receiving a rod to be cut, mounting holes 36, 38 for mounting handle 14 and drive assembly 16 as discussed below, and a central opening 39 which aligns with central opening 30 of plate 18 when the apparatus is assembled.

Still referring to FIG. 3, plate 20 can also have an inset area 42 which receives and holds a cutting blade as will be discussed below.

Figure 4:
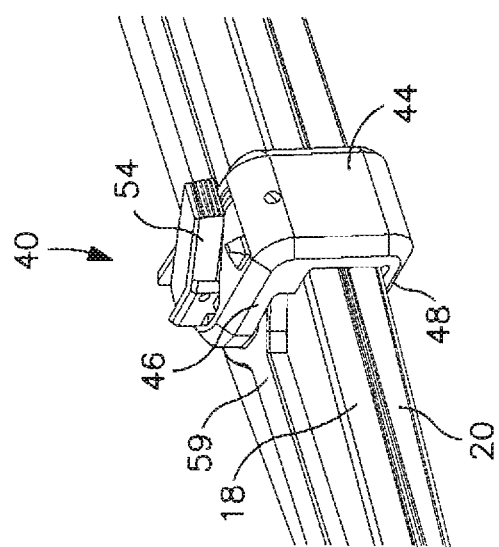
FIGS. 4 and 5 illustrate a latch mechanism for securing the plates of the apparatus of the present invention together, and releasing them as needed.
Figure 5:
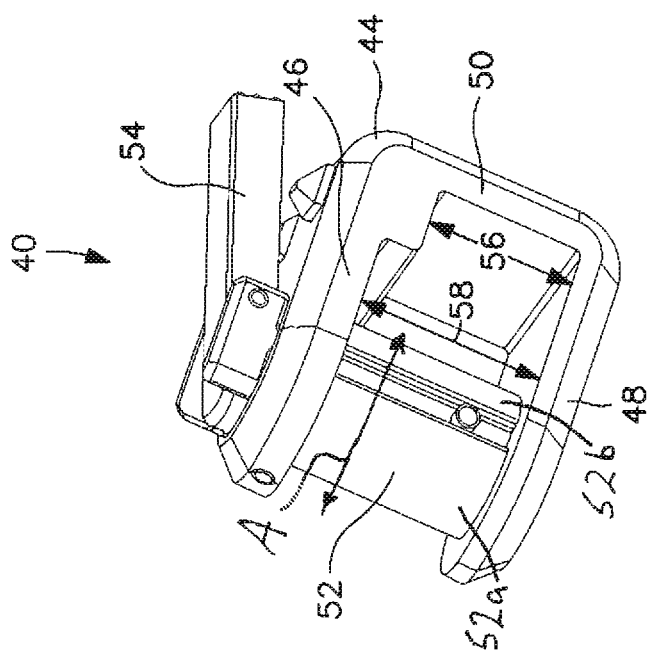

Referring to FIGS. 1, 4 and 5, a fastening assembly 40 is provided for holding plate 18 relative to plate 20. Fastening assembly 40 in this embodiment is a substantially U-shaped bracket 44 which has an upper arm 46 and a lower arm 48 connected to each other through a base 50. A gap is defined between upper arm 46 and lower arm 48 which is sufficient in size to receive plates 18, 20. A pivot post 52 extends from one arm to the other, and when fastening assembly 40 is mounted to the device, pivot post 52 extends through central opening 30 of plate 18 (FIG. 2) and also through central opening 39 of plate 20 (FIG. 3). This serves to pivotably hold plate 18 relative to plate 20 in a way which allows pivot around pivot post 52 of one plate 18 relative to the other plate 20.

Fastening assembly 40 is advantageously a releasable connection so that assembly 40 can be released, and plates 18, 20 separated from each other as needed. In the embodiment shown in FIGS. 4 and 5, a lever or latch 54 can be operated by a user of the apparatus 10 to remove pivot post 52 from at least one of central opening 30 and central opening 39. This advantageously allows one plate 18 to be pivoted relative to the other plate 20, for example to allow access to blades or cutters mounted in inset area 42, and/or openings 24, 28.

FIG. 4 shows an enlarged portion of apparatus 10 according to the invention, with fastener 40 attached around plates 18, 20 as described above. FIG. 5 shows fastening assembly 40 further enlarged, and removed from apparatus 10 to illustrate internal components thereof. As shown, pivot post 52 can advantageously be provided as two post segments 52a, 52b which can move closer and further from each other (schematically illustrated by arrow A, FIG. 5) to either secure plates 18, 20 to each other, or allow pivot post 52 to be extracted from at least one opening 30, 39 so as to release plates 18, 20 from each other for cutter replacement.

Bracket 44 has an internal profile which in one area 56 defines a first gap size between arms 46, 48 which slidingly receives plates 18, 20, and which in a second area 58 defines a second gap size which is defined by a surface of arms 46, 48 which is stepped up away from the other arm to make the second gap larger to accommodate the added thickness of a rib 59 which is provided along plate 18 for added durability. In use, fastener assembly 40 when released allows pivot of plate 18 relative to plate 20 to expose inset area 42 so that a blade mounted therein can easily be replaced.

According to the invention, drive assembly 16 serves to drive one plate 18 relative to the other plate 20 in an oscillating motion which gradually increases in magnitude, and this drives the blade in the same oscillating motion around the rod to be cut, providing a large cutting force, and cutting the rod in a clean cut without requiring the cumbersome procedures needed with conventional rod cutters. Drive assembly 16 includes a handle or crank 60 which is rotated by hand to impart rotation to a drive shaft mounted within a drive housing 62. As will be more thoroughly described below, drive housing 62 rotatable receives a drive shaft in an eccentric sleeve, and rotation of crank 60 drives these two members at slightly different speeds. The drive shaft has an eccentric end which is rotatably engaged with plate 18. During rotation of these two components, the drive shaft gradually is moved off-center from the outer diameter of the eccentric sleeve, resulting in off-center rotation of the eccentric end of the drive shaft, which imparts the desired oscillation to plate 18 relative to plate 20.

Figure 6:
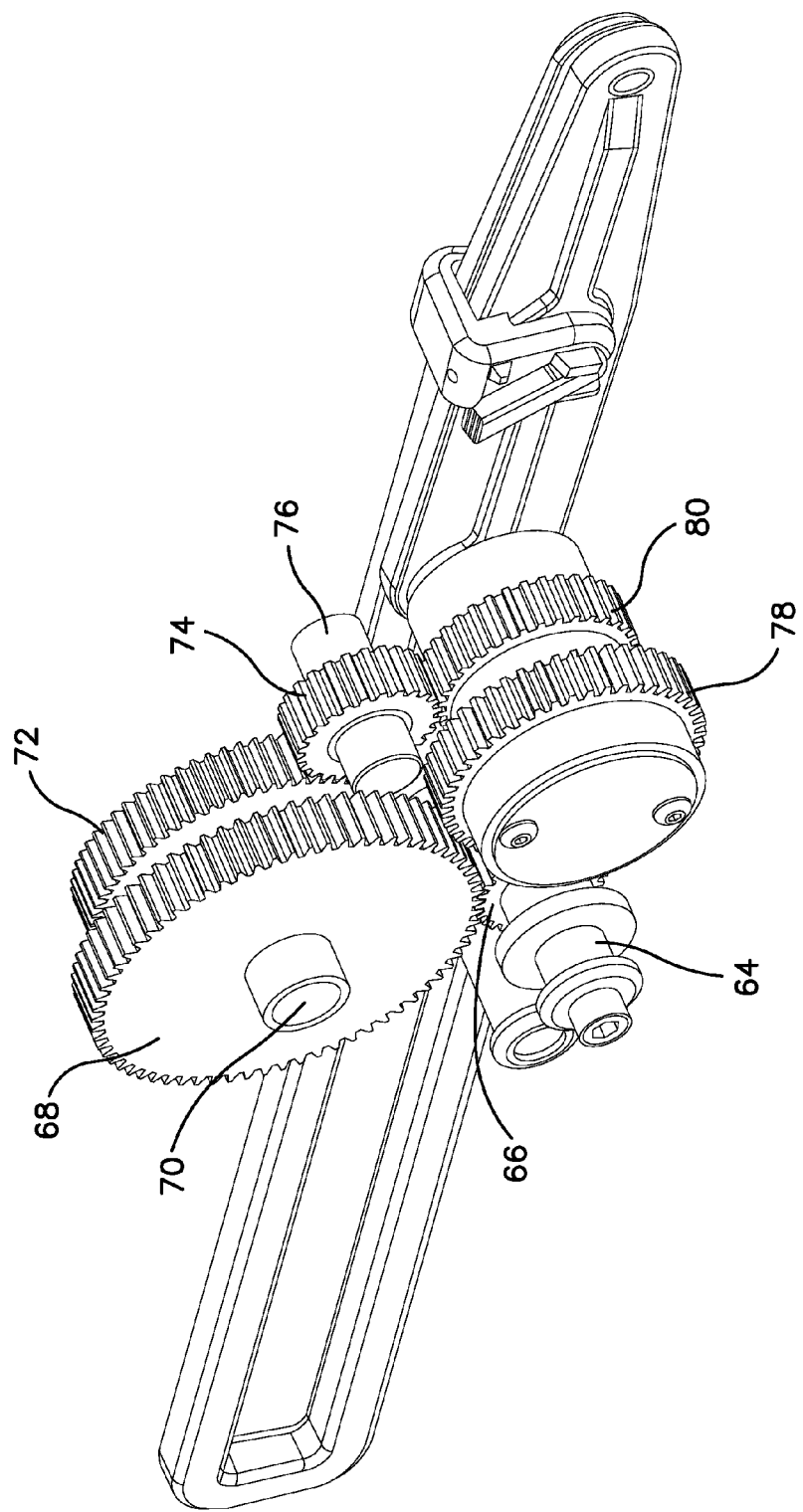
FIG. 6 is a view of an apparatus according to the invention with the drive housing removed to illustrate the drive gears of this embodiment.

Drive assembly 16 is further illustrated in FIGS. 6-14. FIG. 6 shows rod cutter 10 with drive housing 62 removed to illustrate the gears which are used to create two different rotations as desired according to the invention. As shown, rotation of crank 60 (not shown in this figure) rotates shaft 64 and a gear 66 which is carried on shaft 64. Gear 66 is engaged with a gear 68 carried on a shaft 70. Another gear 72 preferably having a diameter which is different from gear 68 is also carried on shaft 70. Gear 72 is engaged with an idler gear 74 which is carried on another shaft 76. Gear 66 is engaged with one driven gear 78, while idler gear 74 is engaged with a second driven gear 80, each of which is carried by a different component of an eccentric shaft assembly 82. It should be readily apparent that with this configuration, rotation of crank 60 and shaft 64 produces rotation of both driven gears 78, 80, at slightly different speeds depending upon the different sizes of gears chosen.

Specifically, rotation of gear 66 in a clockwise direction would rotate both gears 68 and 78 in counter-clockwise direction. Rotation of gear 68 in that counter-clockwise direction turns shaft 70 and also gear 72 in that counter-clockwise direction. This rotation is imparted from gear 72 to idler gear 74, which turns in a clockwise direction. Clockwise rotation of idler gear 74 turns gear 80 in a counter-clockwise direction. Thus, rotation of the crank and shaft 64 in a clockwise direction results in counter-clockwise rotation of both driven gears 78, 80. The different sizes of gears 68, 72, 74, 78 and 80 are selected to create a desired differential in rotation speed responsive to the single rotation of crank and shaft 64.

It should be noted that while a preferred arrangement of gears is described and illustrated, other shapes and configurations of gears could be utilized and still provide the desired rotation of driven gears according to the invention.

Figure 7:
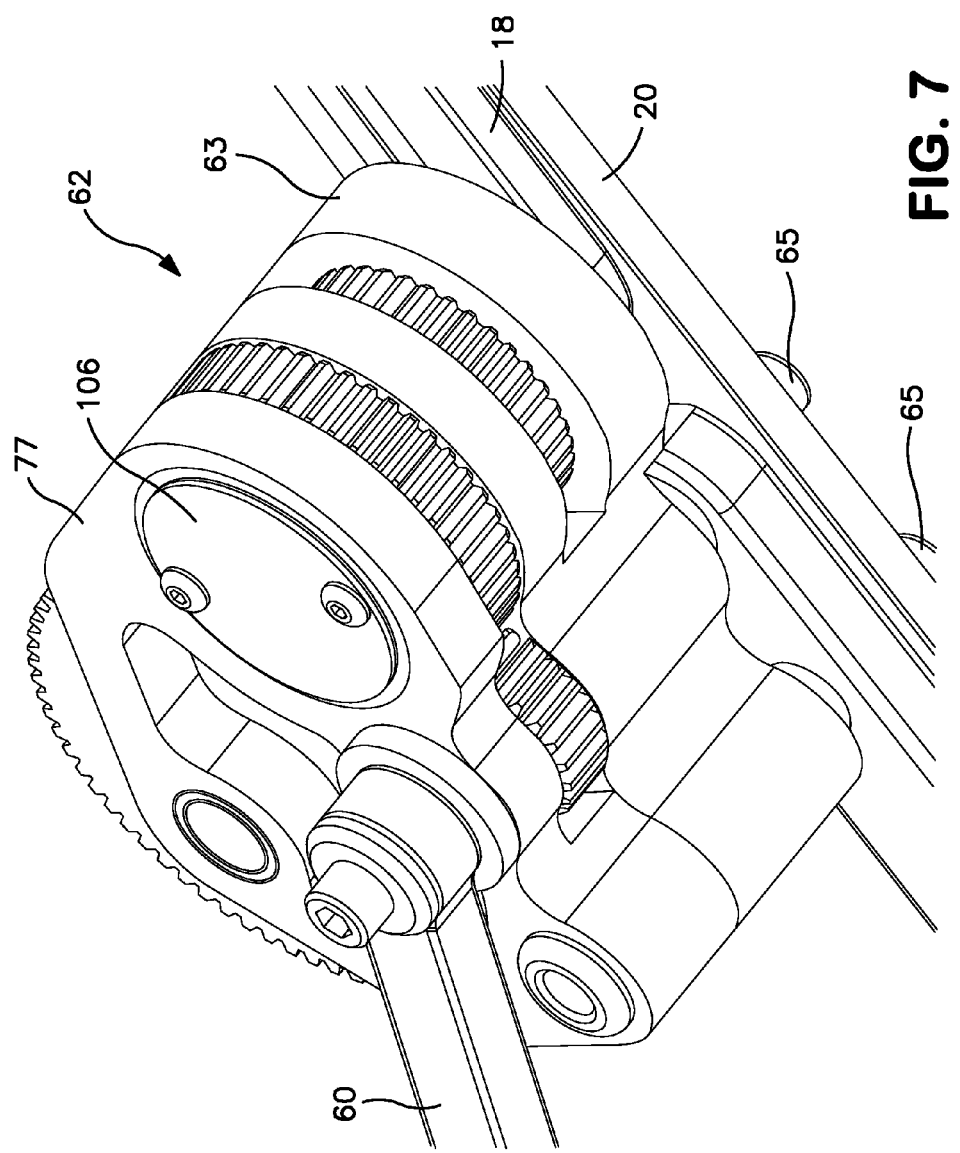
FIG. 7 further illustrates the drive gears and drive housing of the present invention.

FIG. 7 shows another view of drive assembly 16 with drive housing 62 in place holding the various gears as intended. As shown, drive housing 62 is preferably fixedly mounted to plate 20 and handle 14, with an end of the eccentric shaft assembly engaged with plate 18.

Figure 7A:
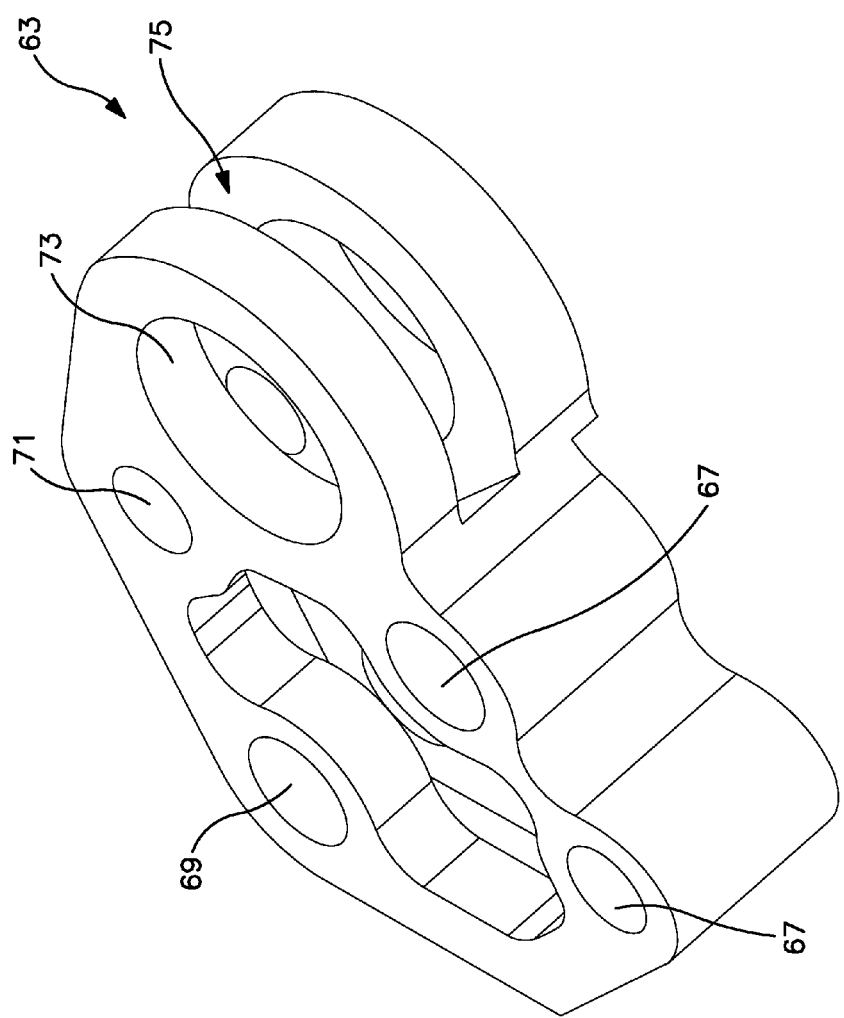
FIGS. 7a and 7b further illustrate the drive housing of the present invention.

Drive housing 62 can advantageously be provided as a housing base 63 (See also FIG. 7a) which is fixed to plate 20 and handle 14 using pins and bolts schematically illustrated at 65. Housing base 63 preferably has one or more holes 67 for fastening pins or the like, one of which can also rotatably receive shaft 64. Housing base 63 is also preferably provided with opening 69 for rotatably receiving shaft 70, opening 71 for rotatably receiving shaft 76, and relatively larger opening 73 for receiving an eccentric shaft assembly 82 as will be discussed below. Housing base 63 according to the invention can also have a split structure at the portion which defines opening 73, and this split structure defines a gap 75 through which gear 80 is exposed when assembled, so that gear 80 can be engaged with idler gear 74 as desired.

Figure 7B:
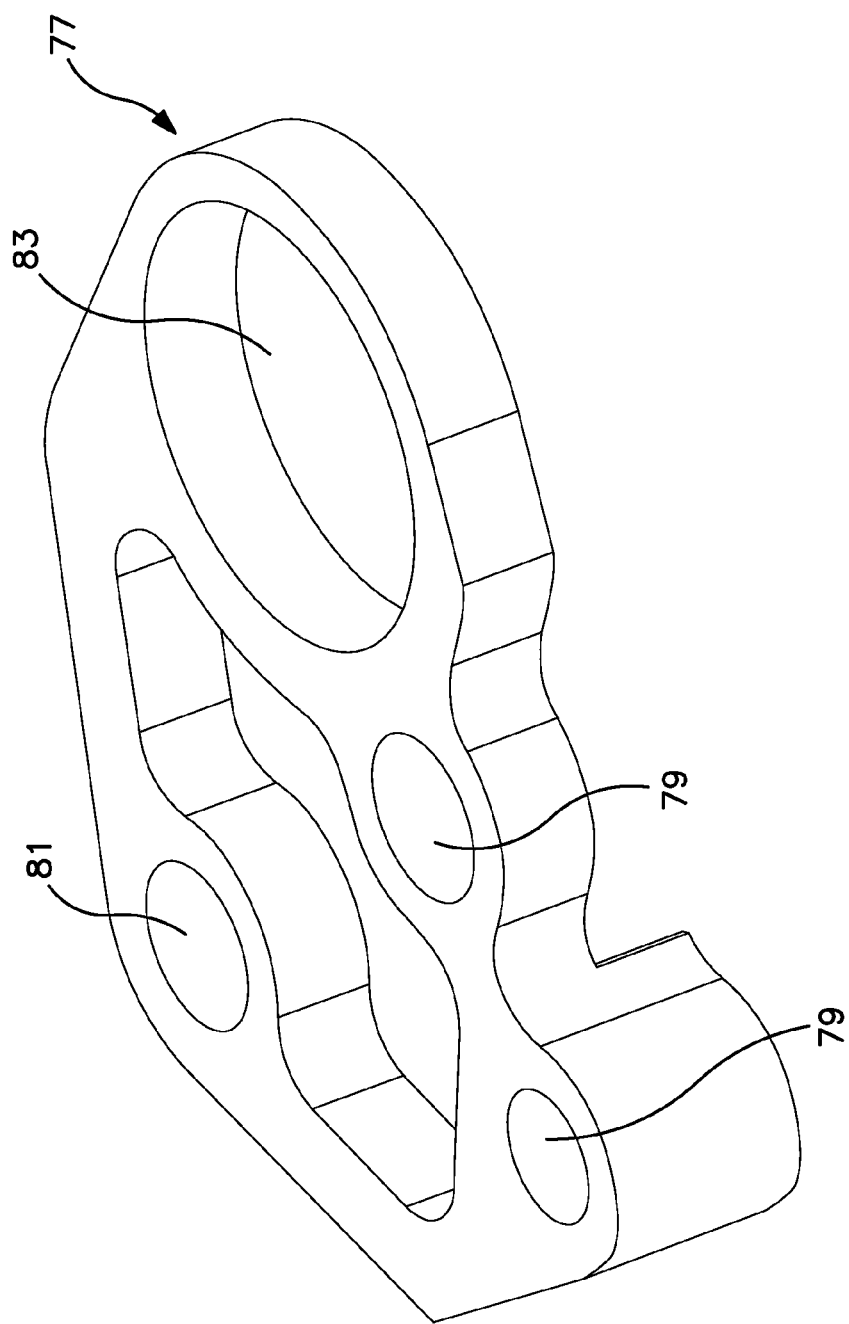

Drive housing 62 also preferably has an upper housing 77 (FIG. 7b) which is designed to be secured over housing base 63, and which preferably has openings 79 aligned with openings 67 of housing base 63 for receiving fasteners and shaft 64. Upper housing 77 also preferably has an opening 81 aligned with opening 69 for rotatably receiving shaft 70, and an opening 83 aligned with opening 73 for rotatably receiving an upper end of eccentric shaft assembly 82.

Figure 9:
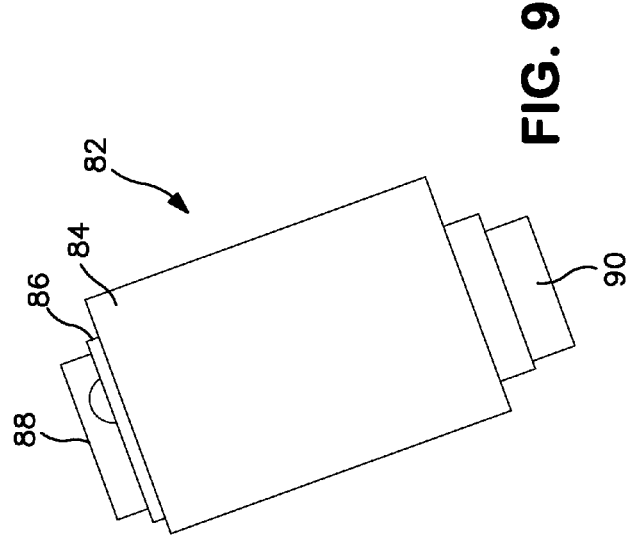
FIGS. 8-10 illustrate the drive shaft assembly of the present invention.
Figure 10:
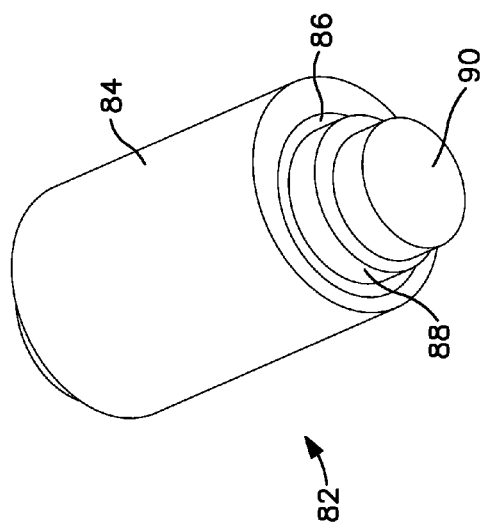
Figure 8:
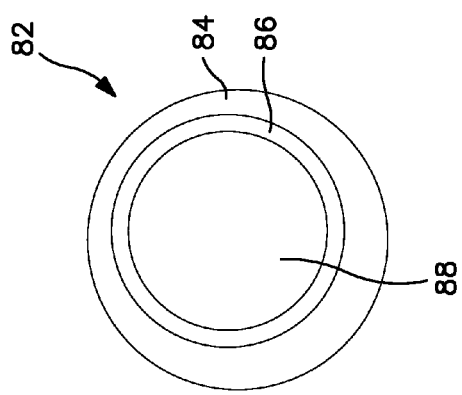

FIGS. 8-14 further illustrate eccentric shaft assembly 82 according to the invention. As shown, eccentric shaft assembly preferably includes an eccentric sleeve 84 which is called eccentric because it has an inner opening which is off center from the center of the outside diameter of sleeve 84. FIG. 8 shows a top view of sleeve 84, with a bushing 86 mounted within the eccentric opening, and with an eccentric drive shaft 88 mounted within bushing 86. FIG. 9 shows this assembly from the side. As seen in this figure, eccentric drive shaft 88 has an end portion 90 which is eccentric, or off-center, from the center of the rest of the shaft. It should be apparent that rotation of sleeve 84 and shaft 88 at different speeds will result in gradual movement of end portion 90 with respect to the center of eccentric sleeve 84 as defined by the outside diameter of sleeve 84. Since end 90 is rotatably engaged with plate 18, this gradual off center movement of end 90 serves to oscillate plate 18 relative to plate 20 as desired.

Referring also to FIG. 11, eccentric sleeve 84 is further illustrated. As shown, this can be a simple hollow cylinder structure, with an eccentric bore 92 or opening passing therethrough. A side opening 94 can also be positioned in sleeve 84 for use in accommodating a key to help engage sleeve 84 with gear 78 as desired.

FIG. 12 shows the detail of a preferred embodiment of eccentric drive shaft 88. As shown, this component can be provided as a simple shaft with end portion 90 extending a short distance from one end. End portion 90 is off center with respect to the outside diameter of shaft 88.

FIGS. 13 and 14 illustrate movement of end portion 90 of eccentric drive shaft 88 relative to the outside diameter of eccentric sleeve 84. FIG. 13 shows what may be a preferred starting position, wherein the eccentricities of sleeve 84 and end portion 90 of shaft 88 are aligned opposite from each other so that rotation of eccentric shaft assembly in the starting position is substantially pure rotation, and the center of the end portion 90 substantially aligned with the center of the eccentric sleeve 84. However, as sleeve 84 and shaft 88 rotate at different speeds, end portion 90 gradually moves off of center, and the resulting rotation of end portion 90 around a circular path drives plate 18 to oscillate relative to plate 20.

Referring to FIG. 12, eccentric drive shaft 88 preferably has a passage 96 arranged passing transverse through a portion of shaft 88, and this passage is engaged by a pin which receives driving motion when handle or crank 60 is rotated.

Figure 15:
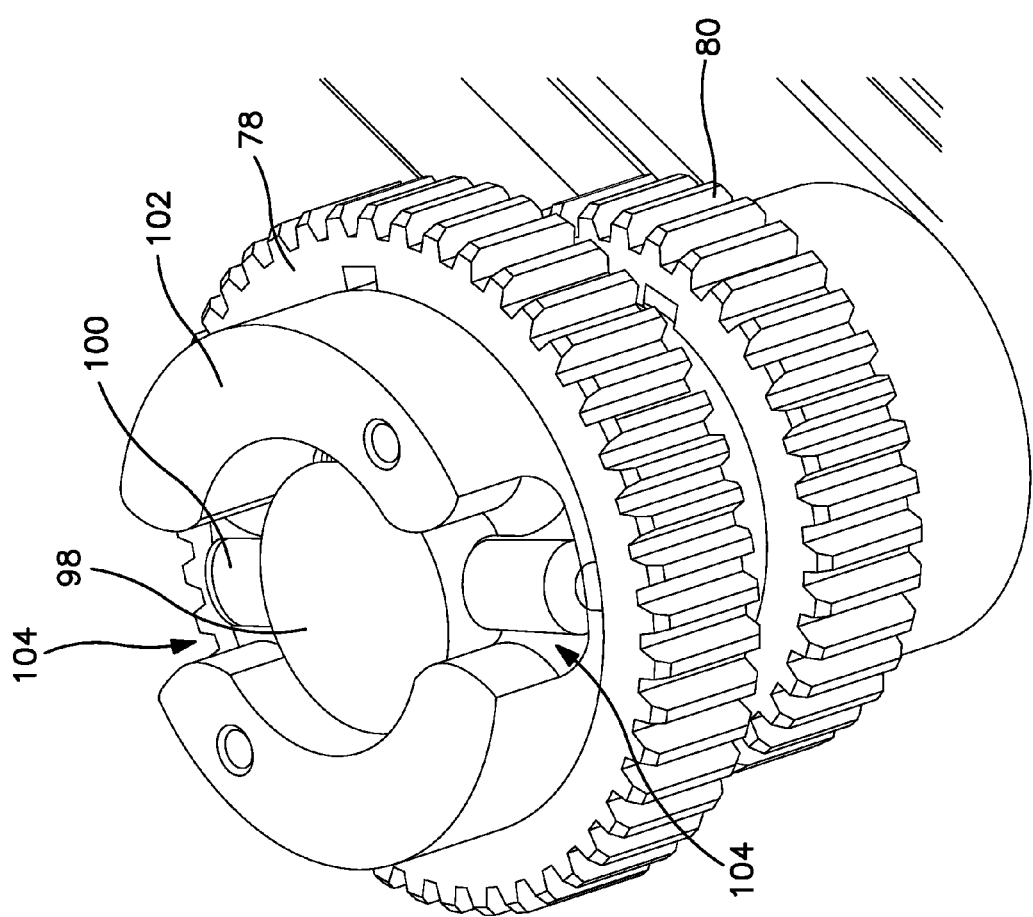
FIG. 15 illustrates one embodiment for engaging a drive gear with the drive shaft according to the invention.

In connection with eccentric shaft assembly 82, it should be noted that rotation of eccentric drive shaft 88 relative to eccentric sleeve 84 requires a drive which accommodates the fact that shaft 88 gradually moves out of central alignment within shaft assembly 82. FIG. 15 shows a sliding drive assembly for driving eccentric drive shaft 88 according to the invention. FIG. 15 shows a top portion 98 of shaft 88, with a pin 100 passing through shaft 88. Gear 78 is engaged with a pin driving collar 102 which is positioned around the upper end of shaft 88, and which has channels 104 through the side wall of collar 102 for receiving pin 100. It should be noted that pin 100 sits freely within channels 104 so that, as shaft 88 rotates out of center with respect to the overall eccentric shaft assembly 82, the upper portion of shaft 88, with pin 100, remains engaged by collar 102 as desired. This simple sliding assembly according to the invention allows reliable engagement of a drive of the device with the relevant gears, while keeping shaft 88 engaged by gear 78 regardless of how far eccentric shaft 88 moves with respect to the overall assembly. Referring to FIG. 7, this view shows a cover 106 which can be attached to collar 102 to close pin 100 within channels 104 of collar 102 as desired, and thereby provide a more stable overall assembly.

Returning to the discussion of gears of the drive assembly, while various configurations can be used to produce the desired different rotation speeds, one non-limiting example is as follows:

Input drive gear 66 has twenty-four (24) teeth.
Gear 68 has sixty-eight (68) teeth.
Gear 72 has fifty-four (54) teeth.
Gear 74 has twenty-four (24) teeth.
Gear 80 has thirty-six (36) teeth.
Gear 78 has forty-five (45) teeth.

With these gear sizes, if gear 78 and the eccentric shaft 88 that it drives via pin 100 rotate 360 degrees, gear 80 and the eccentric sleeve 84 that it drives will rotate 357.36 degrees. It will take 68.2 revolutions of gear 78 to offset the eccentric shaft 88 to the maximum of 180 degrees. Different gear tooth numbers will provide different ratios for different desired results.

Returning to FIG. 3, plate 20 as described above has opening 39 which is aligned with central opening 30 of plate 18, and central opening 30 is preferably elongated as shown. The elongated opening 30 allows for axial movement plate 18 relative plate 20, as well as side to side pivot, and these movements are preferably made around fastening assembly 40 as described above.

Returning to the operation of the drive of the present invention, when eccentric sleeve 84 rotates one revolution, eccentric shaft 88 rotates less than 360 degrees. This pushes shaft 88 and sleeve 84 out of concentric alignment and into an offset position. Subsequent rotations of sleeve 84 move shaft 88 further off center until the maximum offset is achieved and shaft 88 and sleeve 84 are oriented 180 degrees from the starting concentric alignment position. Due to the mechanical advantage, the closer shaft 88 gets to 360 degree rotation per revolution of sleeve 84, the lower the offset and force that shaft 88 drives. However, the lower the offset per revolution, the more revolutions that are required to achieve a 180 degree offset between shaft 88 and sleeve 84. Gear ratios may be changed to achieve a greater or lesser mechanical advantage or a desired number of rotations per 180 degrees of offset.

Figure 16:
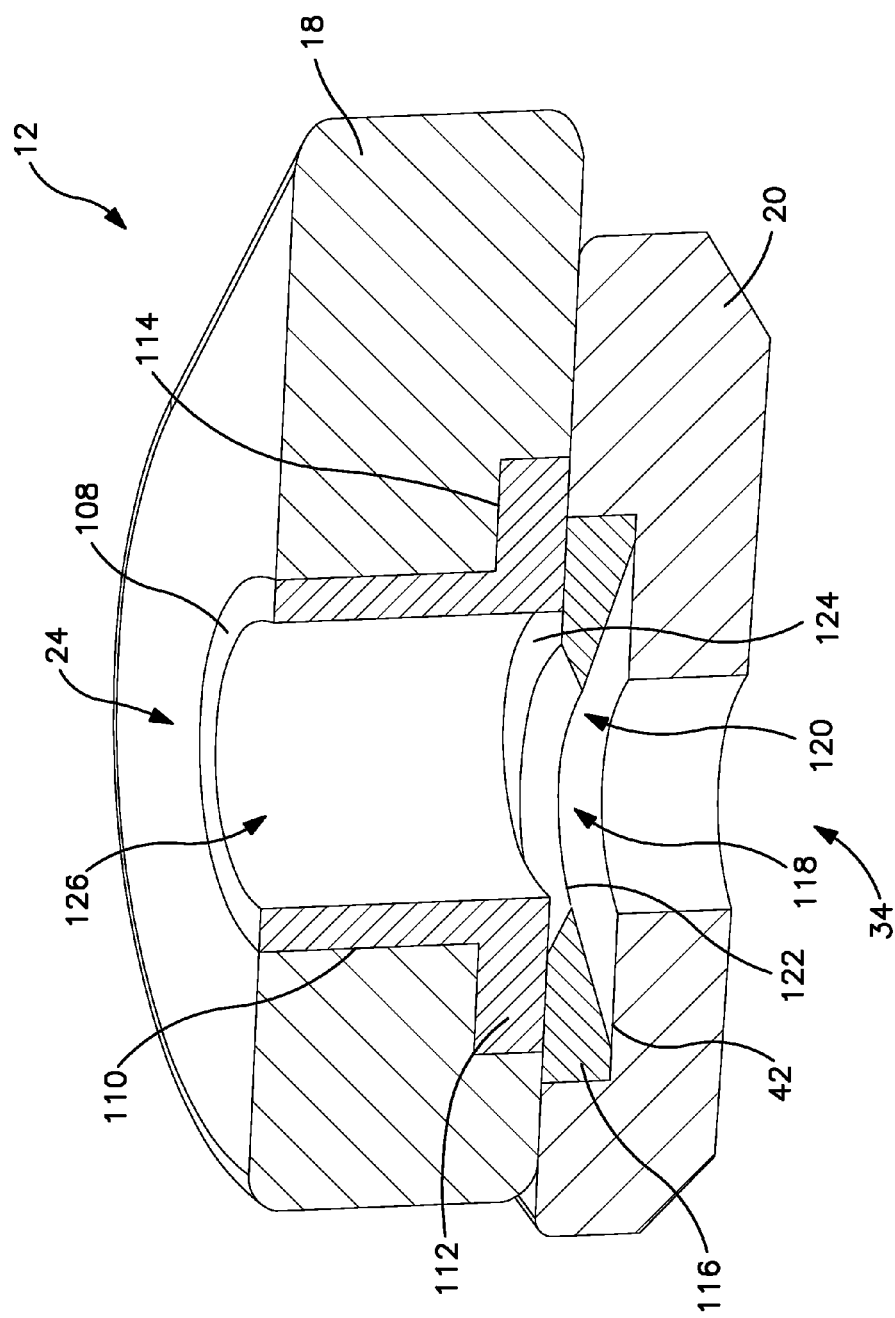
FIG. 16 is a cross section taken along the lines A-A of FIG. 2, and illustrates the cutting assembly according to the invention.
Figure 17:
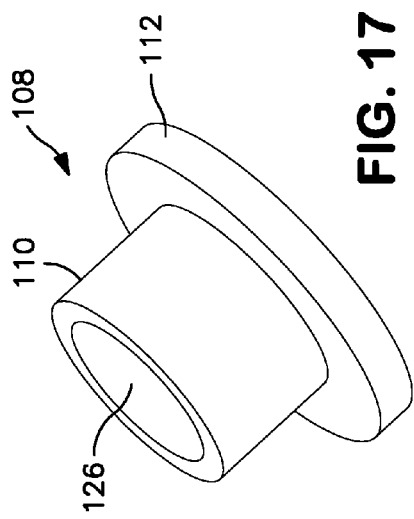
FIGS. 17-19 further illustrate components of the cutting assembly according to the invention.
Figure 18:
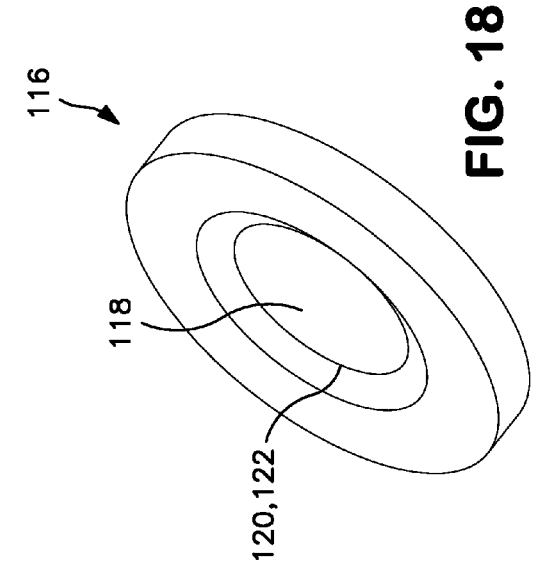

Returning to FIG. 1, rod cutter 10 has, as mentioned, a cutting assembly 12 at one end. FIGS. 16-18 further illustrate components of cutting assembly 12. FIG. 16 is a cross section taken along the lines A-A of FIG. 2, and shows a portion of plates 18 with opening 24, and plate 20 with opening 34. A cutter retainer 108 is positioned within opening 34, preferably rotatably positioned within opening 24. FIG. 17 further illustrates cutter retainer 108 according to the invention. As shown, cutter retainer 108 can advantageously have a substantially cylindrical portion 110 sized to fit for smooth rotation within opening 24. Cutter retainer 108 also preferably has a flange portion 112 which is sized to provide a stable surface against which a cutter insert can oscillate. In this regard, plate 18 can be provided with an inset region 114 (FIG. 16) for receiving flange 112 of cutter retainer 108 as shown. This further serves to stabilize the cutting assembly overall, and also to provide stability to a rod held in the cutting assembly during a cutting procedure.

Figure 19:
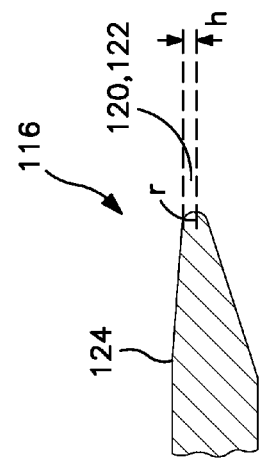

Inset region 42 of plate 20 is sized to hold a cutter insert 116, which can preferably be provided in the form of a substantially flat ring having a central opening 118, and having an edge 120 defining opening 118 wherein edge 120 is a cutting edge for scoring and cutting rods. To this end, edge 120 can advantageously be angled to a point 122 as shown in FIGS. 16 and 18. In larger section as shown in FIG. 19, edge 120 actually has a radius r preferably in the range of about 0.001 to about 0.005 mils, most preferably of about 0.003 mils. Further, this radius is defined at a point below a top flat surface 124 of cutter insert 116, and the distance from top flat surface 124 to a straight horizontal radius of cutting edge 120 is preferably between about 0.003 and about 0.007 mils, most preferably about 0.005 mils. These dimensions provide a cutting edge 120 which is particularly effective at cutting rods made of hard materials such as titanium, and providing a cut which is smooth, while also giving the cutting edge 120 a decent useful life. Cutter insert 116 or at least the cutting edge 120 thereof, can be made from any appropriate material that is well known within the art, such as hardened stainless steel or hardened tool steel or the like.

Cutter retainer 108 and cutter insert 116 are preferably placed freely within opening 24 of plate 18 and opening 34 of plate 20. These components can be placed in the inset areas 42, 114 discussed above, which form counter bores for receiving them. Note that cutter retainer 108 has a central opening 126 for receiving a rod to be cut, and cutter insert 116 also has central opening 118 for receiving the rod to be cut, and oscillation of cutter retainer 108 relative to cutter insert scores edge 120 around the outer surface of the rod with increasing magnitude until the rod is cut. During this cutting, since cutter retainer 108 and cutter insert 116 are rotatable within plates 18, 20, they do actually rotate during cutting, which also helps to provide a clean cut of the rod, and also to avoid the frictional destruction of cutter insert 116. Cutter retainer 108 and cutter insert 116 are preferably replaceable components so that a proper cutting edge may be provided for each use, and may constitute disposable components which are replaced after each use, or as frequently as necessary. It will be appreciated that the pivoting of plates 18, 20 relative to each other provides convenient access to replace the cutter retainer and/or the cutter insert.

Figure 16A:
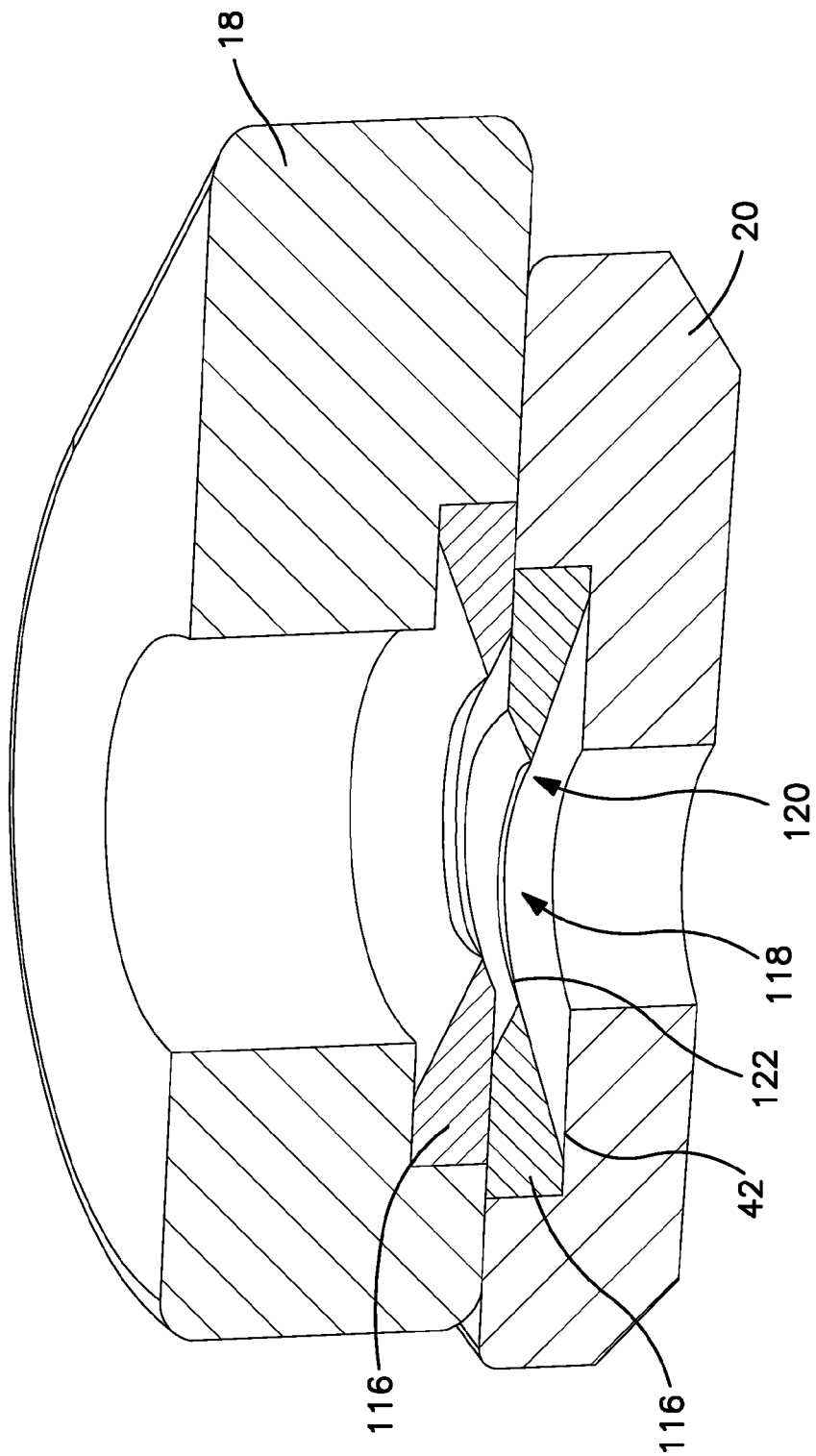
FIG. 16a is a cross section similar to FIG. 16, showing an alternate embodiment.

Referring now to FIG. 16a, an alternate embodiment is shown wherein the cutting assembly includes two cutter inserts 116, one nested in each of plates 18, 20. This provides 2 cutting edges instead of one, and one of the cutting inserts 116 takes the place of cutter retainer 108. The shape of the inset area of plate 18 could be changed accordingly, or could be maintained the same shape to provide the option of using two cutter inserts 116 as shown in FIG. 16a or a cutter insert 116 and cutter retainer 108 as shown in FIG. 16, with the same plates 18, 20.

It should be appreciated that while the illustrated embodiment shows drive of the cutting being powered by a hand crank, the apparatus could likewise be powered by a bevel gear system and could be motor driven, powered by a battery or direct electricity, or in any other manner which would be known to a person skilled in the art.

The rod cutting apparatus of the present disclosure may be used to cut various types of rods, one example of which is a spinal rod. For such a procedure, the cutter is positioned to cut a rod, for example a rod made from titanium, cobalt, implantable plastic, or any other implantable material or the like. This rod is positioned within openings 24, 34, more specifically within central openings 126, 118 of cutter retainer 108 and cutter insert 116, respectively, such as by inserting the end of the rod through openings 24, 34. In the case of a rod for medical use, this may occur away from the patient, such as on a back table, at the side of the patient, or even with the tip of the rod cutter inserted into the incision. Manual or other operation of the crank or shaft attached to the crank begins to drive the drive assembly 16, which in turn oscillates plate 18 relative to plate 20 at a gradually increasing magnitude. As openings 126, 118 oscillate more and more out of alignment, cutting edge 120 scores further into the rod, resulting in a clean cut of the rod, without burrs or sharp ends.

The rod cutter of the present disclosure may be implemented in other possible applications. While the medical arts are a preferred area of use of the rod cutter of the present invention, the rod cutter may also be applied to other technologies such as other mechanical arts and the like, in any application that may benefit from the properties of the present invention.

It should be noted that in the presently disclosed embodiment, since plate 18 holds cutter retainer 108 which also holds the rod to be cut, this plate could be considered the rod holding plate. Further, since plate 20 holds the cutter insert or cutting member, this plate could be considered the blade holding plate. Further, it is within the broad scope of the present invention to have other mechanisms for holding the cutting member in a manner which oscillates the cutting member relative to the rod. Thus, in the broadest sense, two plates might not be needed, as driving mechanisms to translate oscillating movement to the cutting member could be otherwise implemented. With this understanding, the currently disclosed embodiment is seen as a preferred specific manner of carrying out this function.

It is to be understood that the invention is not limited to the illustrations described and shown herein, which are deemed merely illustrative of the best modes of carrying out the invention, and which are susceptible of modification of form, size, arrangement of parts and details of operation. The invention rather is intended to encompass all such modifications, which are within its spirit and scope as defined by the claims.

What is claimed is:

1. A method for cutting a rod using a rod cutter apparatus which comprises a rod holding plate having a rod opening for receiving a rod to be cut; a cutting member having a central opening defined by a cutting edge, the central opening being substantially aligned with the rod opening; and a drive assembly connected between the rod holding plate and the cutting member to cause oscillation of the cutting member relative to the rod holding plate, wherein oscillation of the cutting member relative to the rod holding plate cuts a rod in the rod opening, the method comprising the steps of:

positioning a rod within the rod opening; and oscillating the cutting member relative to the rod holding plate so as to score and cut the rod with the cutting member, wherein the drive assembly comprises a drive shaft having an eccentrically positioned end, and a sleeve having an eccentrically positioned bore, the drive shaft being rotatably positioned within the bore, further comprising a housing mounted to one of the plates and rotatably holding the sleeve of the drive assembly, wherein the eccentrically positioned end of the drive shaft is rotatably engaged with the other of the plates, wherein the drive assembly drives rotation of both the sleeve and the drive shaft relative to the sleeve, and wherein the drive assembly comprises a single driven shaft, a first gear assembly driven by the single driven shaft and engaged with the sleeve for driving rotation of the sleeve, and a second gear assembly driven by the single driven shaft and engaged with the drive shaft for driving rotation of the drive shaft, wherein the first gear assembly and the second gear assembly have different gear ratios so as to rotate the sleeve and the drive shaft at different rates of rotation whereby the drive shaft also rotates relative to the sleeve.

2. The method of claim 1, wherein operation of the drive assembly drives the cutting member around an outside diameter of the rod, scoring the rod with increasing offset of the cutting member relative to the rod, until the rod is cut.

3. A rod cutter apparatus, comprising:
a rod holding plate having a rod opening for receiving a rod to be cut;
a cutting member having a central opening defined by a cutting edge, the central opening being substantially aligned with the rod opening; and
a drive assembly connected between the rod holding plate and the cutting member to cause oscillation of the cutting member relative to the rod holding plate,
wherein oscillation of the cutting member relative to the rod holding plate cuts a rod in the rod opening, wherein the drive assembly comprises a drive shaft having an eccentrically positioned end, and a sleeve having an eccentrically positioned bore, the drive shaft being rotatably positioned within the bore,
further comprising a housing mounted to one of the plates and rotatably holding the sleeve of the drive assembly, wherein the eccentrically positioned end of the drive shaft is rotatably engaged with the other of the plates,
wherein the drive assembly drives rotation of both the sleeve and the drive shaft relative to the sleeve, and
wherein the drive assembly comprises a single driven shaft, a first gear assembly driven by the single driven shaft and engaged with the sleeve for driving rotation of the sleeve, and a second gear assembly driven by the single driven shaft and engaged with the drive shaft for driving rotation of the drive shaft, wherein the first gear assembly and the second gear assembly have different gear ratios so as to rotate the sleeve and the drive shaft at different rates of rotation whereby the drive shaft also rotates relative to the sleeve.

4. The apparatus of claim 3, further comprising a blade holding plate, wherein the cutting member is positioned in the blade holding plate, and wherein the drive assembly causes oscillation of the blade holding plate relative to the rod holding plate.

5. The apparatus of claim 4, wherein the cutting member is rotatably held within the blade holding plate.

6. The apparatus of claim 5, further comprising a cutter retainer rotatably held within the rod holding plate, wherein the cutter retainer has a central opening for receiving the rod to be cut, and wherein the cutting member has a central opening for receiving the rod to be cut, and wherein the central opening of the cutter retainer is substantially aligned with the central opening of the cutting member.

7. The apparatus of claim 6, wherein the rod holding plate has an inset region for receiving the cutter retainer, and wherein the blade holding plate has an inset region for receiving the cutting member.

8. The apparatus of claim 4, further comprising a fastening assembly to movably fasten the rod holding plate relative to the blade holding plate.

9. The apparatus of claim 8, wherein the fastening assembly has a locked position wherein the rod holding plate and the blade holding plate are pivotably fixed relative to each other by the fastening assembly, and an unlocked position wherein one of the rod holding plate and the blade holding plate can be pivoted away from the other of the rod holding plate and the blade holding plate.

10. The apparatus of claim 9, wherein the rod holding plate and the blade holding plate are further held one relative to the other by the drive assembly, and wherein pivot of the one plate relative to the other plate when the fastening assembly is in the unlocked position is around the drive assembly.

11. The apparatus of claim 8, further comprising a mounting hole in one of the plates and a sliding slot in the other of the plates, and wherein the fastening assembly comprises a shaft which, in the locked position, extends from the mounting hole through the sliding slot to allow both pivot and some axial translation of one plate relative to the other plate.

12. The apparatus of claim 3, wherein the cutting member has a cutting edge, and wherein the cutting edge has a radius of between about 0.001 and about 0.005 mils.

13. The apparatus of claim 3, wherein the cutting member has a first surface facing the rod holding plate, and a second surface facing away from the rod holding plate, and wherein the cutting edge is closer to the first surface than the second surface.

14. The apparatus of claim 1, wherein rotation of the drive shaft relative to the sleeve moves the eccentrically positioned end between a start position wherein the eccentrically positioned end is concentric with the sleeve, and a displaced position wherein the eccentrically positioned end is radially offset from a center of the sleeve.

15. The apparatus of claim 14, wherein the drive assembly comprises a gear for imparting rotation to the drive shaft, and wherein the gear is engaged with the drive shaft through a slotted collar connected to one of the gear and the drive shaft, and a rod slidably received in the slotted collar and connected to the other of the gear and the drive shaft.

* * * * *